United States Patent
Zhu et al.

(10) Patent No.: US 7,738,953 B2
(45) Date of Patent: Jun. 15, 2010

(54) METHOD AND DEVICE FOR PREVENTING PLAQUE FORMATION IN CORONARY ARTERIES

(75) Inventors: Qingsheng Zhu, Little Canada, MN (US); Avram Scheiner, Vadnais Heights, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 553 days.

(21) Appl. No.: 11/203,756

(22) Filed: Aug. 15, 2005

(65) Prior Publication Data
US 2005/0283099 A1   Dec. 22, 2005

Related U.S. Application Data

(63) Continuation of application No. 09/852,919, filed on May 10, 2001, now abandoned.

(51) Int. Cl.
*A61N 1/36* (2006.01)

(52) U.S. Cl. .......................................................... 607/2

(58) Field of Classification Search ......... 600/373–375; 607/2, 4, 5, 9, 116, 119, 122, 129
See application file for complete search history.

(56) References Cited

U.S. PATENT DOCUMENTS

| | | | |
|---|---|---|---|
| 4,830,006 A | 5/1989 | Haluska et al. | |
| 4,998,933 A | 3/1991 | Eggers et al. | |
| RE33,925 E | 5/1992 | Bales et al. | |
| 5,178,618 A | 1/1993 | Kandarpa | |
| 5,178,620 A | 1/1993 | Eggers et al. | |
| 5,603,731 A | 2/1997 | Whitney | |
| 5,609,617 A | 3/1997 | Shealy et al. | |
| 5,632,766 A | 5/1997 | Hsu | |
| 5,700,283 A | 12/1997 | Salo | |
| 5,755,761 A * | 5/1998 | Obino | 607/122 |
| 5,792,183 A | 8/1998 | Esler | |
| 5,800,471 A | 9/1998 | Baumann | |

(Continued)

FOREIGN PATENT DOCUMENTS

WO   WO-98/56324   12/1998

(Continued)

OTHER PUBLICATIONS

Chekanov, V., et al., "Use of Electrical Stimulation to Prevent Atherosclerosis in the Abdominal Aorta (Experimental Study)", *Supplement to the Journal of the Americal College of Cardiology*, 35 (2) (Supplement A), Abstract No. 1022-57,(Feb. 2000),p. 244A.

*Primary Examiner*—Carl H Layno
*Assistant Examiner*—Frances P Oropeza
(74) *Attorney, Agent, or Firm*—Schwegman, Lundberg & Woessner, P.A.

(57) ABSTRACT

A method and device for preventing plaque build-up in a coronary artery includes providing an electrical field generating device, and generating an electrical field in the coronary artery to prevent plaque build-up in the coronary artery. The method further includes sensing the heart rhythm and generating the electrical field after a depolarization wave in the heart. The electrical field is generated by circuitry, in one embodiment implanted circuitry, connected to leads which are epicardially or intracardially positioned on the heart.

6 Claims, 3 Drawing Sheets

U.S. PATENT DOCUMENTS

| | | | |
|---|---|---|---|
| 5,843,136 | A | 12/1998 | Zhu et al. |
| 5,871,529 | A | 2/1999 | Bartig et al. |
| 5,876,397 | A | 3/1999 | Edelman et al. |
| 5,876,424 | A | 3/1999 | O'Phelan et al. |
| 5,891,175 | A | 4/1999 | Walmsley et al. |
| 5,944,710 | A | 8/1999 | Dev et al. |
| 6,023,640 | A | 2/2000 | Ross |
| 6,097,986 | A | 8/2000 | Janke et al. |
| 6,129,749 | A | 10/2000 | Bartig et al. |
| 6,148,233 | A | 11/2000 | Owen et al. |
| 6,152,954 | A | 11/2000 | Scheiner et al. |
| 6,178,356 | B1 | 1/2001 | Chastain et al. |
| 6,179,824 | B1 | 1/2001 | Eggers et al. |
| 6,201,991 | B1 | 3/2001 | Chekanov |
| 6,212,428 | B1 | 4/2001 | Hsu et al. |
| 6,212,434 | B1 | 4/2001 | Scheiner et al. |
| 6,216,035 | B1 | 4/2001 | Stahl et al. |
| 6,317,615 | B1 | 11/2001 | KenKnight et al. |
| 6,347,247 | B1 | 2/2002 | Dev et al. |
| 6,560,489 | B2 | 5/2003 | Hauck |
| 6,666,863 | B2 | 12/2003 | Wentzel et al. |

FOREIGN PATENT DOCUMENTS

| | | |
|---|---|---|
| WO | WO-99/42176 | 8/1999 |

* cited by examiner

METHOD AND DEVICE FOR PREVENTING PLAQUE FORMATION IN CORONARY ARTERIES

CROSS-REFERENCE TO RELATED APPLICATION(S)

This application is a continuation of U.S. patent application Ser. No. 09/852,919, filed on May 10, 2001, now abandoned, the specification of which is incorporated herein by reference.

FIELD OF THE INVENTION

The present method relates generally to prevention of plaque formation in arteries and, more particularly, to application of electrical fields to prevent plaque formation in coronary arteries. The present invention also relates to devices for applying electrical fields to prevent plaque formation in arteries.

BACKGROUND

Atherosclerosis is a common disease of the arteries in which fatty material, cholesterol, and other substances, are deposited on the vessel wall, resulting in narrowing and eventual impairment of blood flow through the vessel. Larger accumulations are called atheromas or plaques. The fatty material can eventually erode the wall of the artery, diminish the elasticity of the artery, and interfere with the blood flow. Clots may form around the plaque deposits, further interfering with blood flow. Severely restricted blood flow to the heart muscle leads to symptoms such as angina or chest pain. In such severe cases, treatments are administered to ensure adequate blood flow to the heart. Conventional treatments, including surgery and medications, attempt to treat the plaque after it has adhered to the vessel wall. Surgical treatments include coronary artery bypass grafting, stent implantation, and balloon angioplasty. Medications may be given to control cholesterol, blood pressure, and abnormal heart rhythms in an attempt to lessen the effects of the plaque buildup in the coronary arteries. However, such treatments are not always effective in preventing the more serious complications of atherosclerosis, for example, sudden death by lethal arrhythmia, acute myocardial infarction (MI or heart attack), or unstable angina.

Accordingly, there is a need to provide a method and a device for preventing plaque formation in coronary arteries.

SUMMARY OF THE INVENTION

The present method includes generating an electrical field at the coronary artery, which electrical field acts to slow, and/or prevent, plaque build-up in the coronary arteries. In one embodiment, an implant is inserted into a patient and a lead is positioned adjacent the coronary artery. The implant generates electrical current carried by the lead, which produces the electrical field in which the coronary artery is immersed. In another embodiment, the electrical signals and electrical fields are non-excitatory so that the application thereof does not effect the rhythm of the heart.

A system for reducing and/or preventing plaque build-up in a coronary artery includes an implant having a power source, electrical signal generating circuitry, and leads connected to the electrical signal generating circuitry. The leads apply the electrical field for preventing plaque build-up in the coronary arteries. In one embodiment, the leads include electrodes which are spaced apart from one another in coronary veins. The electrodes produce an electric field, which prevents plaque build-up in coronary arteries which are in the electrical field.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
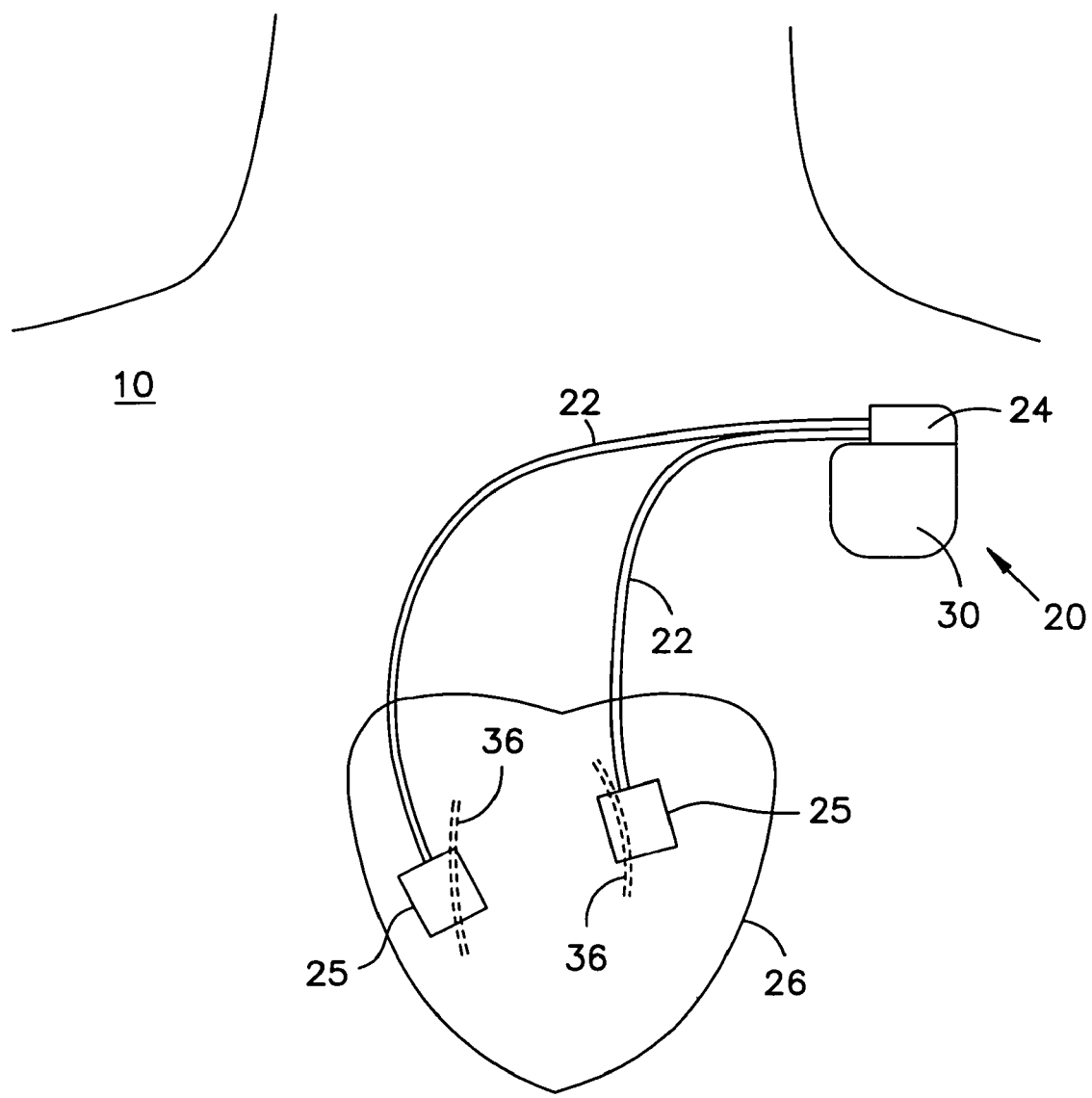
FIG. 1 is a schematic drawing illustrating generally one embodiment of a system according to the present invention and an environment in which it is used.

FIG. 1 is a schematic drawing illustrating, by way of example, one embodiment of a medical device for applying an electrical field to prevent and\or reduce plaque build-up in a coronary artery or vein. The device includes an implant 20 positioned within a human body 10. Leads 22 are electrically and physically coupled through a multiple port socket 24 to housing 30. Leads 22 are epicardial leads each having at least one electrode 25 positioned epicardially on heart 26. The electrodes 25 are patches or meshes placed over an area of a coronary vessel (artery or vein) 36 having an onset of plaque build-up or an area where it is believed plaque build-up may begin. The patch or mesh type electrodes 25 apply the electrical field to the coronary vessel and, in particular to the area of the coronary vessel having the onset of plaque build-up or the area having a high risk of plaque build-up. The electrical field at the artery reduces the adhesion of plaque to the vessel wall and thus reduces the chance of developing atherosclerosis. In some embodiments, the coronary vessel is a coronary artery. In one embodiment, additional leads 22 are provided to provide further coverage of the heart. In another embodiment, the leads 22 each include a plurality of electrodes 25 such that heart 26 is essentially covered by electrodes and most of the coronary arteries are positioned within an electric field to prevent plaque build-up.

The implant 20 includes the main housing 30 in which a power source and electrical signal generating circuitry are encased and hermetically sealed suitable for implantation in a body cavity. Housing 30 is a metal or metal alloy construction, e.g. titanium or titanium alloy, or other biocompatible housing materials. The power source and circuitry will be explained in greater detail below. In one embodiment, the electrical field is produced between the electrodes 25 and the housing 30. In another embodiment, the electrical field is produced between electrodes 25. In yet another embodiment, each electrode patch 25 includes at least one anode and cathode for producing the electrical field.

Figure 2:
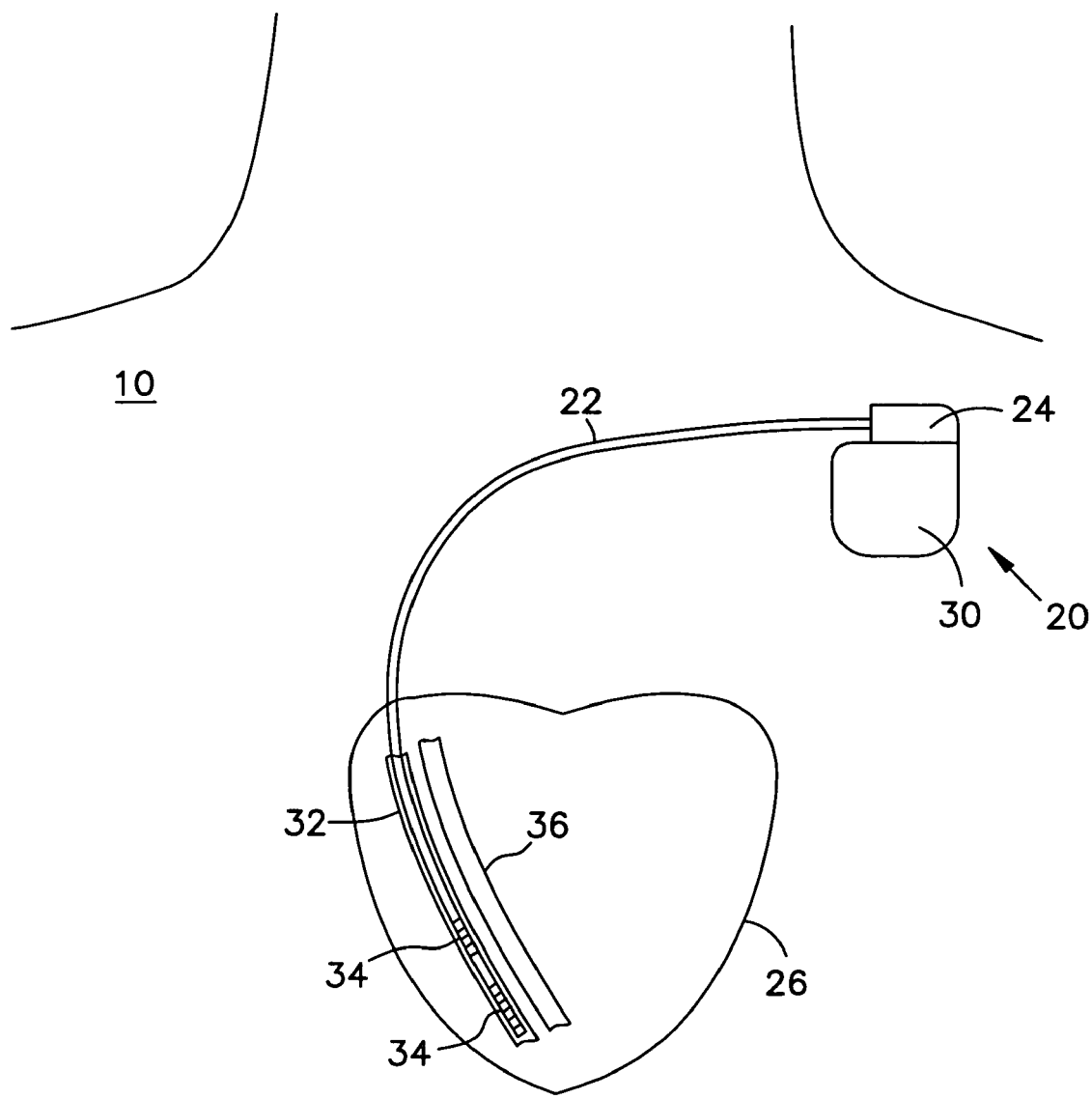
FIG. 2 is a schematic drawing illustrating another embodiment of the present invention.

FIG. 2 shows another embodiment of the medical device for preventing plaque build-up in coronary arteries. A single lead 22 is at least partially intracardially positioned within a cardiac vein 32. The lead 22 includes at least one electrode 34, here shown as two electrodes, which receives an electrical signal and generates an electrical field which transmits through the wall of vein 32 and enters artery 36. The electrical field at the artery reduces the adhesion of plaque to the artery wall and thus reduces the chance of developing atherosclerosis. In the embodiment with two electrodes 34, the electrical field is generated between the two electrodes such that some of the current passed therebetween passes through the coronary artery. It will be understood that a plurality of intracardial leads 22 could be attached to implant 20 and positioned within a plurality of veins 32 to prevent plaque build-up in a plurality of coronary arteries 36 that are subjected to the electrical field produced by electrodes 34.

In some embodiments, the leads include the characteristics of the leads described in U.S. Pat. Nos. 6,212,434; 6,178,356; 6,152,954; 6,148,233; 6,129,749; 6,097,986; and 5,871,529, all assigned to the assignee of the present application and all incorporated by reference for any purpose.

Figure 3:
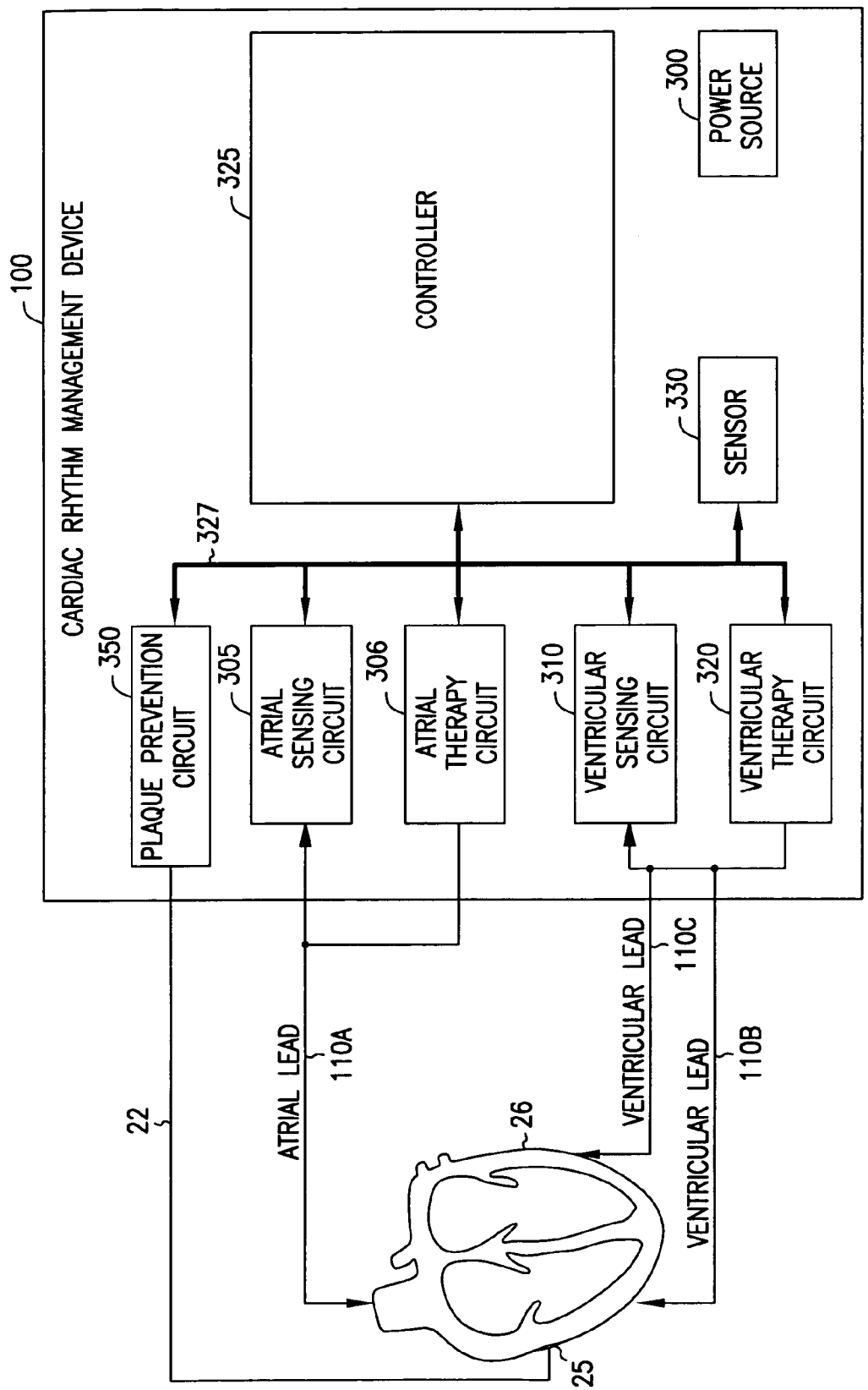
FIG. 3 is a schematic diagram illustrating an implant.

FIG. 3 shows another embodiment with the medical device for preventing plaque formation or build-up in coronary arteries being integral with a cardiac rhythm management device 100. Cardiac rhythm management devices 100, which can be internal or external devices, provide therapy to a patient's heart to correct various forms of arrhythmia, such as tachyarrhythmias and bradyarrhythmias. Examples of cardiac rhythm management devices include pacemakers, defibrillators, and devices with combinations of both pacing functions and defibrillating functions. Device 100 includes a power source 300, an atrial sensing circuit 305, an atrial therapy circuit 306, a ventricular sensing circuit 310, a ventricular therapy circuit 320, and a controller 325.

Atrial sensing circuit 305 is coupled by atrial lead 110A to heart 26 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the sensed atrial heart signals. Such signals provided to controller 325 indicate, among other things, the presence of atrial fibrillation.

Atrial therapy circuit 306 provides atrial pacing therapy, as appropriate, to electrodes located at or near one of the atriums of heart 26 for obtaining resulting evoked atrial depolarizations. In one embodiment, atrial therapy circuit 306 also provides cardioversion/defibrillation therapy, as appropriate, to electrodes located at or near one, or both, of the atriums of heart 26, for terminating atrial fibrillation and/or other atrial arrhythmia.

Ventricular sensing circuit 310 is coupled by ventricular leads 110B, 110C to heart 26 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Ventricular sensing circuit 310 provides one or more signals to controller 325, via node/bus 327, based on the received ventricular heart signals. Such signals provided to controller 325 indicate, among other things, the presence of ventricular depolarizations, whether regular or irregular in rhythm.

Ventricular therapy circuit 320 provides ventricular pacing therapy, as appropriate, to electrodes located at or near one of the ventricles of heart 26 for obtaining resulting evoked ventricular depolarizations. In one embodiment, ventricular therapy circuit 320 also provides cardioversion/defibrillation therapy, as appropriate, to electrodes located at or near one, or both, of the ventricles of heart 26, for terminating ventricular fibrillation and/or other ventricular tachyarrhythmias.

Controller 325 controls the delivery of therapy by ventricular therapy circuit 320 and/or other circuits, based on heart activity signals received from atrial sensing circuit 305 and ventricular sensing circuit 310. Controller 325 includes various modules, which are implemented either in hardware or as one or more sequences of steps carried out on a microprocessor or other controller. It is understood that the various modules of controller 325 need not be separately embodied, but may be combined and/or otherwise implemented, such as in software/hardware. In an embodiment, the controller 325 includes a memory in which is stored default parameters and a processor which uses the parameters stored in memory and sensed data to control various therapies.

In general terms, sensing circuits 305 and 310 sense electrical signals from heart tissue in contact with the catheter leads 110A-C to which these sensing circuits 305 and 310 are coupled. Sensing circuits 305 and 310 and/or controller 325 process these sensed signals. Based on these sensed signals, controller 325 issues control signals to therapy circuits, such as atrial therapy circuit 306 and/or ventricular therapy circuit 320, if necessary, for the delivery of electrical energy (e.g., pacing and/or defibrillation pulses) to the appropriate electrodes of leads 110A-C. Controller 325 may include a microprocessor or other controller for execution of software and/or firmware instructions. The software of controller 325 may be modified (e.g., by remote external programmer) to provide different parameters, modes, and/or functions for the implantable device 100 or to adapt or improve performance of device 100.

In one further embodiment, one or more sensors, such as sensor 330, may serve as inputs to controller 325 for adjusting the rate at which pacing or other therapy is delivered to heart 26. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Device 100 further includes a plaque prevention circuit 350 which is connected, via node/bus 327, to controller 325. Plaque prevention circuit 350, in response to control signals from controller 325, generates electrical signals transmitted by lead 22 to electrodes 25 or 34. In one embodiment, controller 325 powers the plaque prevention circuit 350 after a depolarization wavefront (P-waves or R-waves) is sensed by one of atrial sensing circuit 305 or ventricular sensing circuit 310. The controller 325 is programmed to link the activation of plaque prevention circuit 350 to either the atrial or the ventricular depolarization so that the electrical field produced by the signal from circuit 350 does not interfere with the heart's natural rhythm or a rhythm induced by the pacing functions of device 100. The circuit 350 is thus energized during the refractory period of the heart rhythm. Consequently, the device including cardiac rhythm management functions and plaque build-up prevention functions produces both excitatory signals (atrial and ventricular therapy circuits 306 and 320) and non-excitatory cardiac signals (plaque prevention circuit 350).

The plaque prevention circuit 350 limits the frequency and the energy in the plaque prevention electrical field. In one embodiment, the frequency is limited to less than the low end of a normal heart rate range. For example, the frequency of plaque prevention signals is limited to a low rate such as one pulse every 10 seconds or one pulse per minute. In another embodiment, the frequency is about 30 to 60 pulses per minute. In some embodiments, the pulse frequency is less than about 1.5 Hz. In some embodiments, the pulse frequency is less than about 1 Hz. Limiting the frequency of the plaque prevention signals reduces the chance of interfering with the rhythm of the heart while still reducing plaque build-up in the coronary arteries within the plaque prevention electrical field. On another embodiment, the energy in the electrical field is less than the electrical energy of a heart stimulation signal. Limiting the energy (current and/or voltage) in the electrical field prevents the electrical field from stimulating heart muscle and interfering with heart function. That is, the electrical field while not capture the heart tissue and dictate a heart rhythm. Moreover, limiting the energy in the electrical field minimizes its effect on the life of power source 300.

Power source 300 is a chemical battery providing electrical power to device 100 for operating the controller 325, powering sensor circuits 305, 310, and 330, powering pacing and defibrillation therapies administered, as needed, by atrial therapy circuit 305 and ventricular therapy circuit 320. Power source 300 further powers the plaque prevention circuit 350 to generate electrical fields for prevention of plaque build-up in coronary arteries.

While the above describes one embodiment of a medical device with which the teachings herein may be performed, it is recognized that other embodiments of implantable medical devices may be used. In some embodiments, the teachings described herein are used in conjunction with the medical devices described in at least one of U.S. Pat. Nos. 6,216,035; 6,212,428; 5,891,175; 5,876,424; 5,843,136; 5,800,471; 5,792,183; 5,700,283; and 5,632,766, all assigned to the assignee of the present application and all are incorporated herein by reference for any purpose.

The illustrated embodiments in FIGS. 1-3 schematically show the positioning of leads 22 and electrodes 25 and 34. Some specific locations of the electrodes may yield more plaque prevention than others. It should be noted, however, that no anatomy is precisely the same and the positioning may not yield as good as a result for one person as compared to another. One specific positioning of electrodes is placing one lead and electrode in the anterior vein and placing another lead and electrode in the lateral vein. The electrical signal is produced between the two electrodes and a non-heart-excitatory signal passes through the left marginal artery and the anterior interventrical artery. Other positions of electrodes and leads are within the scope of the present disclosure.

A brief description of one embodiment is provided to more completely portray the method and device from preventing plaque build-up in coronary arteries. The device 100 is implanted into the body cavity 10, with atrial lead 110A electrically connected to the atrium and ventricular leads 110B and 110C respectively electrically connected to the left and right ventricles. Plaque prevention lead 22 is epicardially placed on heart 26 over a coronary artery 36. The coronary artery 36 has the beginnings of plaque formation or is a suspected location for future plaque formation. The controller 325 receives various inputs from sensors 330 and sensing circuits 306 and 320, and based on these inputs provides, as needed, pacing signals and defibrillation signals through leads 110A-110C. Controller 325 controls operation of plaque prevention circuit 350, which provides a non-excitatory electrical signal to lead 22. Lead 22 transmits the electrical signal to electrode 25, which creates an electrical field at coronary artery 36. The electrical field created by electrode 25 includes a low voltage, low current electrical signal which at least partially flows through the coronary artery 36. Low voltage is less than four volts in one embodiment and less than three volts in another embodiment. The electrical field prevents formation or reduces growth of plaque on the wall of the coronary artery.

The present description uses the phrase "electrical field" to describe the phenomena which prevents plaque build-up in the coronary artery. One form of the electrical field is current flowing from one electrode to another electrode or to the housing of the implant. It is believed that the current blocks the fatty material, cholesterol, and other substances from adhering to the arterial wall and to other substances already adhered to the arterial wall. The electrical field, consequently, prevents formation of or addition to plaques in the artery.

In some embodiments, the signals applied by the present device to prevent plaque build-up in arteries include those signals described in U.S. Pat. No. 6,201,991 issued to Chekanov on Mar. 13, 2001, which is herein incorporated by reference.

In some embodiments, the signals applied by the present device for the prevention of plaque buildup in coronary arteries includes adjusting the signal strength to provide a stronger signal during the refractory period and a lower strength signal during the non-refractory period. For example, a typical pacing signal pulse width is about 0.5 milliseconds. The signal has a potential of about 0.5 volt if it is applied to a lead having a good contact, e.g. low resistance and high conductivity, to the patient's tissue. In situations where the contact is poor, then the signal has a potential of greater than 0.5 volt to compensate for the poor contact. In some embodiments, the signal potential is about 1 volt. In some embodiments, the signal potential is about 1-2 volts. In some embodiments, the signal potential is about less than or equal to about 10 volts. In some embodiments, the signal strength applied to the heart tissue is about 0.5 volts or less for pacing. It is desirable to not interfere with the heart's natural rhythm or a paced rhythm while using the present device to prevent plaque build-up. Accordingly, the signal strength for the prevention of plaque buildup is limited to the signal strength applied by a cardiac rhythm management circuit.

The present device is not so limited during the refractory period of the heart rhythm. In some embodiments, higher strength signals are applied during the refractory period. That is, signals for the prevention of plaque buildup may exceed the pacing voltages. The signals for prevention of plaque buildup, in an embodiment, exceed 10 volts. Such a signal is directed to the location where it is desired to prevent plaque buildup and not directed to the heart tissue whereat such a signal could capture the heart rhythm.

The present method and apparatus is described in applications involving implantable medical devices. However, it is understood that the present methods and apparatus may be employed in unimplanted medical devices. Moreover, while a method and system to prevent plaque build-up in coronary arteries is described above, it is within the scope of the present invention to apply the method and system to prevent plaque build-up in coronary veins as well.

CONCLUSION

The device according to the present disclosure positions electrodes adjacent coronary arteries to produce electrical fields which prevent or reduce growth of plaque build-up in the arteries. The electrodes are positioned epicardially on the heart or intracardially in a coronary vein. The electrodes are adjacent the coronary arteries in need of plaque build-up prevention. The electrical fields produced by the device do not excite the heart so as to not interfere with the heart rhythm. In one embodiment, the device includes elements for sensing heart depolarizations and elements for controlling heart function. The device may provide its non-excitatory signals at a very low rate (one signal per 10 seconds or one signal per minute). In one embodiment, the electrical field is generated by passing a low current between two electrodes with some of the current passing through the coronary artery. The epicardial electrodes are positioned spaced from each other on the heart. The intracardial electrodes are positioned in one vein or the electrodes are positioned in different veins. In sum, non-excitatory electrical fields are provided to prevent plaque build-up in coronary arteries.

What is claimed is:

1. A method comprising:
    identifying an atherosclerotic or potentially atherosclerotic region in a patient's coronary artery;
    implanting an implantable cardiac device having electrical stimulation and sensing circuitry connectable to electrodes;
    disposing one or more sensing electrodes connected to the sensing circuitry in a cardiac location for detecting cardiac electrical activity;
    disposing one or more stimulation electrodes in a location for directing an electrical field at the identified atherosclerotic region;
    programming a controller of the cardiac device to deliver electrical stimulation to the stimulation electrodes at an energy below a capture threshold of the myocardium and in a manner that directs an electrical field to the atherosclerotic region to prevent plaque formation.

2. The method of claim 1 further comprising programming the controller to deliver electrical stimulation to the stimulation electrodes at an energy above the capture threshold of the myocardium during a cardiac refractory period as determined from detected cardiac activity.

3. The method of claim 1 further comprising disposing one or more stimulation electrodes into a cardiac vein to direct current toward the identified atherosclerotic region.

4. The method of claim 1 further comprising disposing the stimulation electrode in the form of a patch applied to the epicardium.

5. The method of claim 1 further comprising disposing a pair of stimulation electrode incorporated into a lead into a cardiac vein and delivering the electrical stimulation as bipolar stimulation.

6. The method of claim 1 further comprising disposing a stimulation electrode into a cardiac vein and delivering the electrical stimulation as unipolar stimulation with a device housing used as an additional electrode.

* * * * *